US012788420B2

(12) United States Patent
Sharma et al.

(10) Patent No.: US 12,788,420 B2
(45) Date of Patent: Nov. 10, 2026

(54) DEVICE AND METHOD FOR MECHANICAL THROMBECTOMY

(71) Applicant: BOSTON SCIENTIFIC MEDICAL DEVICE LIMITED, Galway (IE)

(72) Inventors: Deepak Kumar Sharma, Muzaffarnagar (IN); Hitendra Purohit, Pune (IN)

(73) Assignee: Boston Scientific Medical Device Limited, Galway (IE)

( * ) Notice: Subject to any disclaimer, the term of this patent is extended or adjusted under 35 U.S.C. 154(b) by 28 days.

(21) Appl. No.: 19/222,463

(22) Filed: May 29, 2025

(65) Prior Publication Data

US 2026/0053519 A1 Feb. 26, 2026

Related U.S. Application Data

(63) Continuation of application No. 18/156,035, filed on Jan. 18, 2023, now Pat. No. 12,336,726.

(60) Provisional application No. 63/363,140, filed on Apr. 18, 2022.

(51) Int. Cl.
*A61B 17/22* (2006.01)
*A61B 17/00* (2006.01)

(52) U.S. Cl.
CPC .................. *A61B 17/22031* (2013.01); *A61B 2017/00367* (2013.01); *A61B 2017/22079* (2013.01)

(58) Field of Classification Search
CPC ........ A61B 17/22031; A61B 17/22032; A61B 2017/00367; A61B 2017/22079; A61B 2017/22034; A61B 2017/22035; A61B 2017/22041; A61B 2017/22045
USPC ................ 606/209, 208, 207, 206, 205, 159
See application file for complete search history.

(56) References Cited

U.S. PATENT DOCUMENTS

2022/0378433 A1* 12/2022 Smith .................... A61B 17/10
2023/0225740 A1* 7/2023 Sharma ................ A61B 17/083
606/142

* cited by examiner

*Primary Examiner* — Jocelin C Tanner
(74) *Attorney, Agent, or Firm* — Fay Kaplun & Marcin, LLP

(57) ABSTRACT

A device includes a catheter extending longitudinally from a proximal end to a distal end and including a lumen and a grasper. The grasper includes jaws connected such that the jaws are movable between an open configuration and a closed configuration. Also, the device includes a control member connected to the grasper so that a longitudinal movement of the member relative to the catheter moves the grasper between the configurations and a proximal interface including a piston connected to the proximal end so that, when the grasper is moved toward the closed configuration, the piston applies a negative pressure through the catheter to draw a separated portion of thrombus proximally therethrough.

14 Claims, 6 Drawing Sheets

DEVICE AND METHOD FOR MECHANICAL THROMBECTOMY

PRIORITY CLAIM

The present application is a Continuation of U.S. patent application Ser. No. 18/156,035 filed on Jan. 18, 2023; which claims priority to U.S. Provisional Patent Application Ser. No. 63/363,140 filed on Apr. 18, 2022. The disclosures of the above application(s)/patent(s) are incorporated herewith by reference.

FIELD

The present disclosure relates to endovascular devices and related methods and, in particular, relates to a surgical device and a related method for mechanically removing a thrombus.

BACKGROUND

Blood clots may disrupt the normal flow of blood to various parts of the body, resulting in life-threatening conditions such as pulmonary embolism or an acute stoke. During some current thrombectomy procedures (removal of a blood clot from within an artery or vein), a catheter may be guided through a blood vessel under image guidance, until the catheter is positioned adjacent a blood clot. The blood clot may then be removed from the blood vessel via any of a variety of methods including, aspiration through the catheter or via a mechanical removal device such as, for example, a stent retriever, which is pushed out of the catheter to capture the blood clot. Devices requiring continuous aspiration, however, may in some cases result in excessive blood loss and/or increased negative pressure, which may lead to the collapse of blood vessels and/or clogging of the catheter. In addition, some mechanical thrombectomy devices require costly and time-consuming procedures involving multiple insertions/removals of the device to achieve complete removal of a thrombus.

SUMMARY

The present disclosure relates to a device for performing a thrombectomy. The device includes a catheter extending longitudinally from a proximal end to a distal end and including a lumen extending therethrough; a grasper mountable over the distal end of the catheter, the grasper including first and second jaws connected to one another such that the first and second jaws are movable between an open configuration, in which the first and second jaws extend about opposing portions of the distal end of the catheter and are separated from one another to receive a portion of a thrombus therebetween, and a closed configuration, in which the first and second jaws are moved toward one another to grasp the portion of thrombus therebetween and separate a grasped portion of thrombus from a remaining portion of the thrombus; a first control member connected to the grasper so that a longitudinal movement of the first control member relative to the catheter moves the grasper between the open and closed configurations; and a proximal interface including a piston connected to the proximal end of the catheter so that, when the grasper is moved toward the closed configuration, the piston applies a negative pressure through the catheter to draw a separated portion of thrombus proximally therethrough.

In an embodiment, the device further includes a second control member connected to the grasper so that a longitudinal movement of the second control member relative to the catheter moves the grasper between the open and closed configurations, the first control member connected to the first jaw of the grasper and the second control member connected to the second jaw of the grasper.

In an embodiment, each of the first and second jaws includes teeth extending therealong, the teeth configured to penetrate the portion of thrombus grasped between the first and second jaws.

In an embodiment, the first and second jaws of the grasper are connected to one another via hinges that bias the grasper toward the closed configuration so that the first and second jaws are maintained in the open configuration via an exterior surface of the catheter when the grasper is mounted over the catheter and revert toward the closed configuration when the grasper is moved distally off of the catheter.

In an embodiment, the grasper includes a covering extending over portions of each of the first and second jaws to define a substantially solid surface thereof so that any portions of thrombus grasped between the first and second jaws are prevented from escaping distally therefrom.

In an embodiment, the device further includes an outer shaft extending longitudinally along an exterior surface of the catheter, the first control member extending through the outer shaft from the proximal interface to the grasper.

In an embodiment, the proximal interface further includes a cylindrical housing connected to the proximal end of the catheter and within which the piston is slidably movable and a crank shaft connected to the piston and to a proximal end of the first control member so that a distal movement of the first control member relative to the catheter moves the grasper toward the closed configuration and the piston proximally within the cylindrical housing to create a negative pressure within the catheter, and a proximal movement of the first control member relative to the catheter moves the grasper toward the open configuration and the piston distally within the cylindrical housing.

In an embodiment, the proximal interface further including a rotating handle connected to the crank shaft so that a rotation of the rotating handle moves the grasper between the open and closed configurations.

In an embodiment, the proximal interface further including a thrombus collecting element connected to the cylindrical housing via a one-way valve, the separated portion of thrombus moved into the thrombus collecting element as the grasper is moved toward the open configuration.

In addition, the present disclosure relates to a device for performing a thrombectomy. The device includes a catheter extending longitudinally from a proximal end to a distal end and including a lumen extending therethrough; a grasper mountable over the distal end of the catheter, the grasper including first and second jaws connected to one another such that the first and second jaws are movable between an open configuration, in which the first and second jaws extend about opposing portions of the distal end of the catheter and are separated from one another to receive a portion of a thrombus therebetween, and a closed configuration, in which the first and second jaws are moved toward one another to grasp the portion of thrombus therebetween and separate a grasped portion of thrombus from a remaining portion of the thrombus; first and second control members extending from distal ends connected to the first and second jaws of the grasper, respectively, to proximal ends, the first and second control members configured such that a longitudinal movement of the first and second control members relative to the catheter moves the grasper between the open and closed configurations; and a proximal interface including a cylindrical housing connected to the proximal end of the catheter and a piston slidably received within the cylindrical so that, when the grasper is moved toward the closed configuration, the piston is moved proximally within the cylindrical housing to apply a negative pressure through the catheter, drawing a separated portion of thrombus proximally therethrough.

In an embodiment, the proximal interface further including a crank shaft connected to the piston and to a proximal end of the first and second control members so that a distal movement of the first and second control members relative to the catheter moves the grasper toward the closed configuration and the piston proximally within the cylindrical housing, and a proximal movement of the first and second control members relative to the catheter moves the grasper toward the open configuration and the piston distally within the cylindrical housing.

In an embodiment, the proximal interface further including a rotating handle connected to the crank shaft so that a rotation of the rotating handle moves the grasper between the open and closed configurations.

In an embodiment, the proximal interface further including a thrombus collecting element connected to the cylindrical housing via a one-way valve, the separated portion of thrombus moved into the thrombus collecting element as the grasper is moved toward the open configuration.

In an embodiment, the each of the first and second jaws include teeth extending therealong, teeth of the first jaw extending toward teeth of the second jaw so that the teeth penetrate a portion of thrombus grasped between the first and second jaws.

In an embodiment, the first and second jaws are biased toward the closed configuration, the first and second jaws maintained in the open configuration via an exterior surface of the catheter when the grasper is mounted over the catheter, and reverting toward the closed configuration when the grasper is moved distally off of the catheter.

In addition, the present disclosure relates to a method for performing a thrombectomy including inserting a catheter through a blood vessel until a grasper mounted over a distal end of the catheter in an open configuration is adjacent a target thrombus within the blood vessel, first and second jaws of the grasper extending over opposing portions of the catheter in the open configuration so that a first portion of the target thrombus is received between the first and second jaws; moving the grasper toward a closed configuration so that the grasper is moved distally off of the catheter and the first and second jaws are moved toward one another to grasp the first portion of the thrombus received therebetween, thereby separating the first portion of thrombus from a remaining portion of thrombus, a negative pressure applied through the catheter as the grasper is moved toward the closed configuration so that the first portion of thrombus is drawn proximally through the catheter; and moving the grasper toward the open configuration by drawing the grasper proximally over the distal end of the catheter, the first portion of thrombus escaping into a thrombus collecting bag as the grasper is moved toward the open configuration.

In an embodiment, the method further includes moving the catheter, with the grasper mounted thereover in the open configuration, distally within the blood vessel so that a second portion of thrombus is received between the first and second jaws of the grasper; moving the grasper toward the closed configuration so that the grasper is moved distally off of the catheter and the first and second jaws are moved toward one another to grasp the second portion of the thrombus received therebetween, thereby separating the second portion of thrombus from a remaining portion of thrombus, a negative pressure applied through the catheter as the grasper is moved toward the closed configuration so that the second portion of thrombus is drawn proximally through the catheter; and moving the grasper toward the open configuration by drawing the grasper proximally over the distal end of the catheter, the second portion of thrombus escaping into the thrombus collecting bag as the grasper is moved toward the open configuration.

In an embodiment, teeth of the first and second jaws penetrate the first portion of thrombus as the grasper is moved toward the closed configuration to separate the first portion of thrombus from the remaining portion of thrombus.

In an embodiment, the negative pressure is applied through the catheter via a piston moving proximally within a cylindrical housing connected to a proximal end of the catheter so that the first portion of thrombus is drawn proximally into the cylindrical housing.

In an embodiment, the first portion of thrombus escaped into the thrombus collecting bag as the piston is moved distally within the cylindrical housing.

BRIEF DESCRIPTION

DETAILED DESCRIPTION

Figure 1:
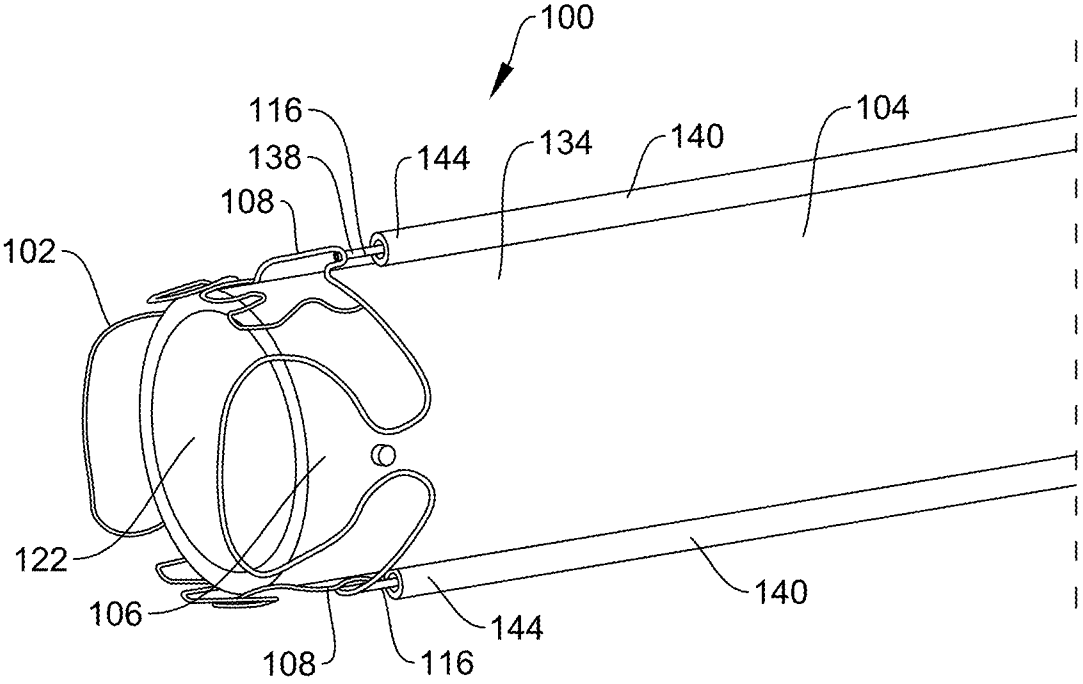
FIG. 1 shows a perspective view of a distal portion of a device according to an exemplary embodiment of the present disclosure, a grasper of the device in an open configuration.

The present disclosure may be further understood with reference to the following description and the appended drawings, wherein like elements are referred to with the same reference numerals. The present disclosure relates to a thrombectomy device and, in particular, relates to a mechanical thrombectomy device configured to systematically grasp and remove portions of a thrombus, while remaining in a target area of a blood vessel, until the entirety of the thrombus has been removed therefrom. Exemplary embodiments of the present disclosure describe a thrombectomy device comprising a grasper mounted over a distal end of a catheter that is insertable through a blood vessel to a target area within the blood vessel. The grasper is movable between an open configuration, in which jaws of the grasper are mounted over the distal end of the catheter and are separated from one another to receive a portion of a thrombus therein, and a closed configuration, in which the jaws of the grasper are moved distally off of the catheter so that the jaws are moved toward one another to grasp the portion of the thrombus received therebetween and separate this grasped portion from the rest of the thrombus.

A proximal interface connected to a proximal end of the catheter includes a piston which, when the grasper is moved toward the closed configuration, applies negative pressure within the catheter so that the separated portion of thrombus is drawn proximally through the catheter into a cylindrical housing of the piston. Upon drawing of the separated portion of thrombus into the cylindrical housing, the grasper may be moved proximally back over the distal end of the catheter to reopen the jaws of the grasper. As the grasper is moved back toward the open configuration, the piston is moved distally within the cylindrical housing, pushing the separated portion of the thrombus into a thrombus collection container connected to the cylindrical housing. The grasper may be moved between the open and closed configurations—grasping portions of the thrombus, separating these portions from the overall thrombus, and removing these portions of thrombus from the blood vessel—until the entire thrombus has been removed from the target area of the blood vessel. Once the entire thrombus has been collected in the collection container, the thrombectomy device may be removed from the target area of the blood vessel. It will be understood by those of skill in the art that terms proximal and distal, as used herein, are intended to refer to a direction toward and away from, respectively, a user of the device.

Figure 2:
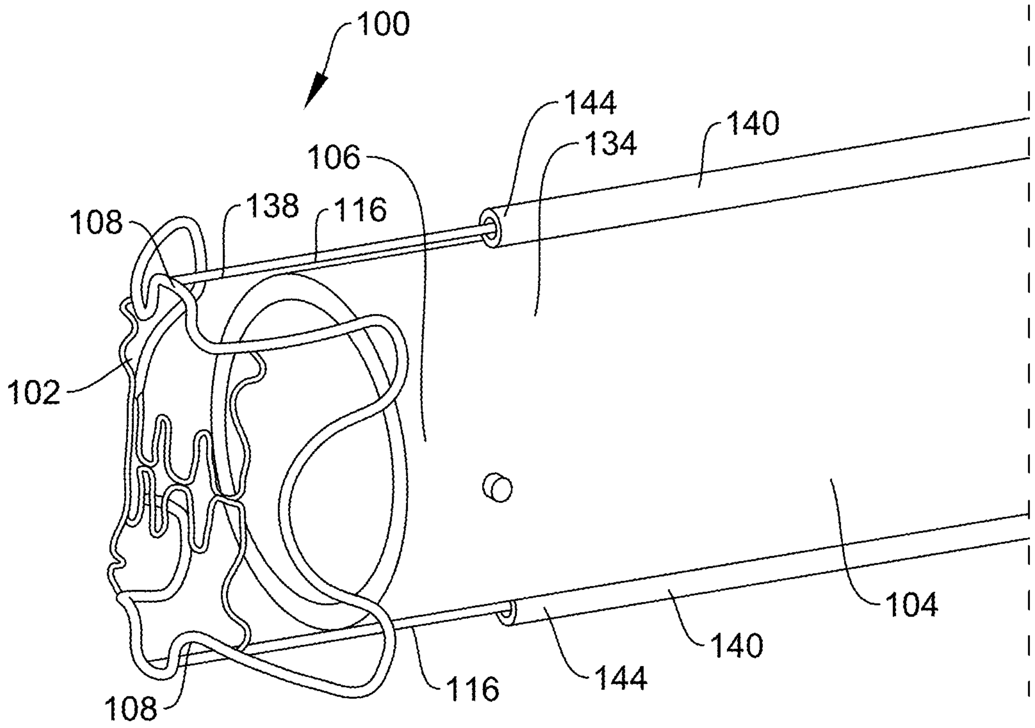
FIG. 2 shows a perspective view of the distal portion of the device according to FIG. 1, the grasper of the device in a closed configuration.

As shown in FIGS. 1-13, a thrombectomy device 100 according to an exemplary embodiment comprises a grasper 102 mountable over a distal end 106 of a catheter 104, and configured to be inserted through a blood vessel to a target area to remove a thrombus therein. The grasper 102 is movable between an open configuration (shown in FIG. 1), in which the grasper 102 is mounted over the distal end 106 of the catheter 104 so that jaws 108 of the grasper 102 are separated from one another, and a closed configuration (shown in FIG. 2), in which the grasper 102 is moved distally off of the catheter 104 so that the grasper 102 reverts toward a biased configuration in which the jaws 108 are moved toward one another to grip and sever material received between the jaws 108 (e.g., a portion of a thrombus).

The exemplary device 100 further comprises a proximal interface 110 connected to a proximal end 112 of the catheter 104 via a cylindrical housing 114, and to the grasper 102 via control members 116. The grasper 102 is moved between the open and closed configurations via the control members 116. With the jaws 108 in the open configuration, the catheter 104 is advanced to a position adjacent to the thrombus and the jaws 108 are moved distally off of the catheter 104 to close over a portion of the thrombus. That is, when the grasper 102 is moved toward the closed configuration, the jaws 108 grasp the portion of the thrombus therebetween and sever the grasped portion from the rest of the thrombus, taking a "bite" of the thrombus. As the grasper 102 is moved toward the closed configuration, a piston 118 slidably moves proximally within a cylindrical housing 114 generating negative pressure through the catheter 104 that draws the separated portion of the thrombus into and through the catheter 104 until this portion of the thrombus enters the cylindrical housing 114 so that the severed/separated portion of thrombus may be "swallowed".

The grasper 102 may then be moved back into the open configuration by drawing the grasper 102 proximally over the distal end 106 of the catheter 104 so that the catheter 104 forces the jaws 108 apart from one another. As the grasper 102 is moved into the open configuration, the piston 118 is moved distally within the cylindrical housing 114, pushing the separated portion of thrombus into a thrombus collecting bag 120 connected thereto. The grasper 102 may be repeatedly moved between the open and closed configurations—grasping, separating, and collecting portions of the thrombus with each iteration—until the entirety of the thrombus has been removed from the blood vessel and collected within the thrombus collecting bag 120. That is, the grasper 102 systematically "bites" and "swallows" portions of the thrombus until the entire thrombus has been removed.

The catheter 104 extends longitudinally from the distal end 106 to the proximal end 112 and includes a lumen 122 extending therethrough. The catheter 104 is sized, shaped, and configured to be inserted through a target blood vessel. As will be understood by those of skill in the art, the catheter 104 should be sufficiently flexible to be inserted through the target blood vessel to a target area therewithin without inflicting undue trauma to the blood vessel or surrounding tissues. While the distal end 106 of the catheter 104 is inserted into the target blood vessel, a proximal portion of the catheter 104 including the proximal end 112 remains outside the body accessible to a user (e.g., surgeon) of the device 100. In an exemplary embodiment, the proximal portion of the catheter 104 also includes a port 124 in communication with the lumen 122 so that tools or devices such as, for example, a dilator, may (if so desired) be inserted into the port 124 and through the lumen 122 to the target area during the thrombectomy procedure.

Figure 3:
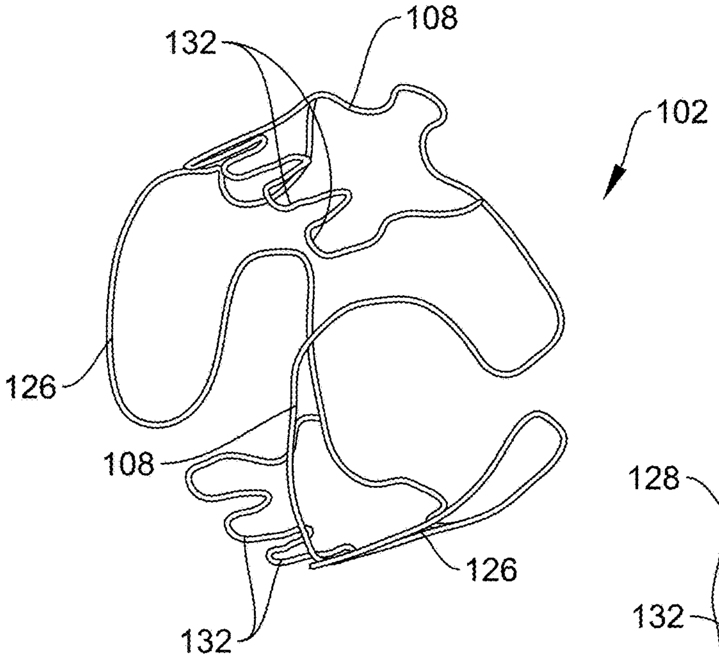
FIG. 3 shows a perspective view of the grasper according to the device of FIG. 1, in the open configuration.
Figure 4:
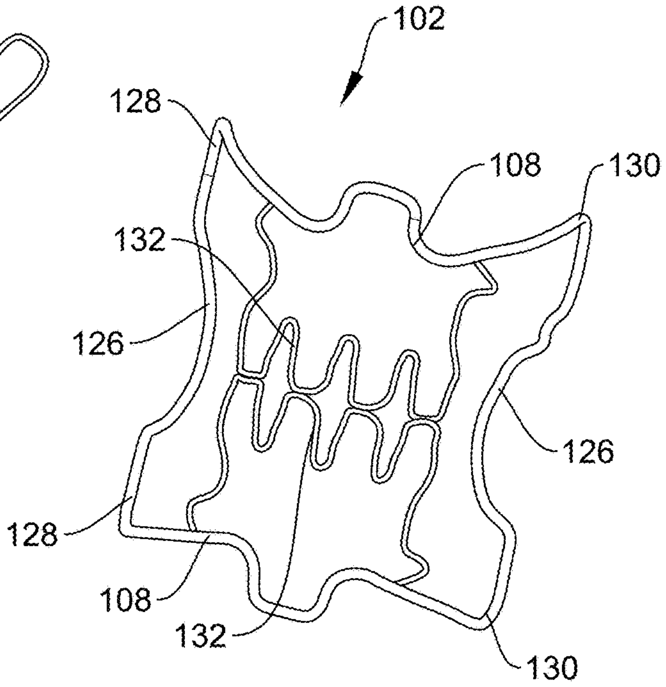
FIG. 4 shows a perspective view of the grasper according to the device of FIG. 1, in the closed configuration.

As shown in FIGS. 3-4, the grasper 102 includes a pair of jaws 108, each of the jaws 108 connected to one another via hinges 126. In one embodiment, each of the jaws 108 extends along a curve from a first end 128 to a second end 130 so that a first one of the hinges 126 connects the first ends 128 of the jaws 108 to one another while a second one of the hinges 126 connects the second ends 130 of the jaws 108 to one another. In an exemplary embodiment, the hinges 126 are spring biased, biasing the jaws 108 toward the closed configuration (FIG. 4) in which the jaws 108 are moved toward one another. Each of the jaws 108 of this embodiment includes teeth 132 or other structural features configured to penetrate and sever a portion of the thrombus from the rest of the thrombus as the jaws 108 are drawn together.

In one embodiment, the teeth 132 of one of the jaws 108 contact the teeth 132 of the other jaw 108. In particular, in the closed configuration, the jaws 108 extend toward one another so that a portion of the thrombus grasped between the teeth 132 of each of the jaws 108 is separated from a remaining portion of the thrombus for removal from the target blood vessel. When the grasper 102 is mounted over the distal end 106 of the catheter 104 in the open configuration, the jaws 108 are positioned on diametrically opposed portions of an exterior surface 134 of the distal end 106 so that the exterior surface 134 of the catheter 104 maintains the grasper 102 in the open configuration with the jaws 108 separated from one another (FIG. 3).

Thus, when the grasper 102 is mounted over the distal end 106 of the catheter 104, the catheter 104 may be positioned relative to the thrombus so that, as grasper 102 is moved distally off of the catheter 104, a portion of the thrombus is positioned between the closing jaws 108. When the grasper 102 is moved distally off of the catheter 104, the grasper 102 is freed to close under the natural bias of the hinges 126. It will be understood by those of skill in the art that the hinges 126 and/or jaws 108 of the grasper 102 may be formed of any of a variety of materials so long as the hinges 126 bias the jaws 108 toward the closed configuration, as described above, and so that the bias is sufficiently strong to cause the teeth 132 to penetrate the thrombus. In one example, portions of the grasper 102 (e.g., the hinges 126) are formed of a shape memory alloy such as, for example, Nitinol to provide and/or add to the bias toward the closed configuration.

Figure 5:
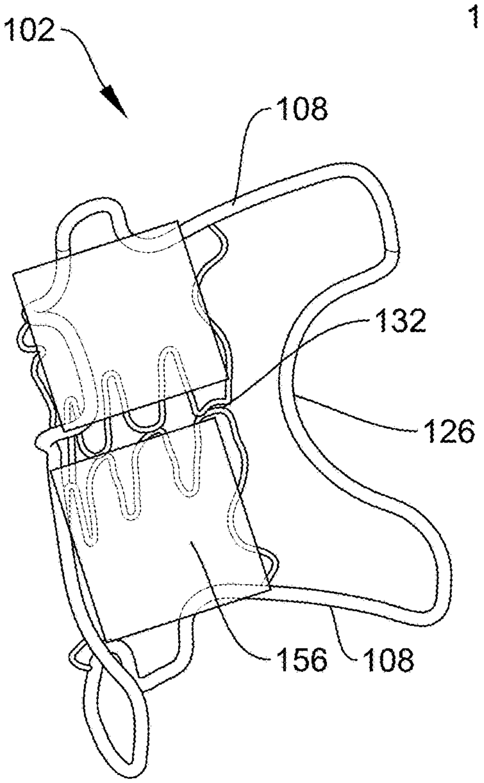
FIG. 5 shows a perspective view of a grasper according to a further embodiment of the device of FIG. 1.

According to a further embodiment, as shown in FIG. 5, the grasper 102 includes a surface or covering 156 extending over portions of the jaws 108 which, when the grasper 102 is in the closed configuration, prevents the grasped portion of thrombus from escaping distally through openings in the distal faces of the jaws 108 (i.e., the covering 156 substantially closes the surface of the jaws 108 that faces distally when the jaws 108 are closed). In this embodiment, the grasper 102 may be formed of additional materials such as, for example, a polymer, which defines and/or covers portions of the jaws 108 to form a substantially solid surface or covering 156. Thus, upon grasping of a portion of the thrombus, the grasped portion is separated from a remaining portion of the thrombus and prevented from escaping distally therefrom so that the severed portion of the thrombus may be drawn into the catheter 104.

Thus, as will be described in further detail below, the separated portion of thrombus is removed from the blood vessel and drawn into the catheter 104 via negative pressure applied through the lumen 122 of the catheter 104 as described above. Although the exemplary embodiment specifically describes the jaws 108 of the grasper 102 as being formed of nitinol and/or a polymer, it will be understood by those of skill in the art that the grasper 102 may be formed out of any of a variety of bio-compatible materials so long as the jaws 108 are configured to grasp and separate a portion of thrombus from a remaining portion of thrombus for removal from the blood vessel.

According to an exemplary embodiment, the device 100 comprises a pair of control members 116 with each control member 116 extending along a length of the catheter 104 from a proximal end 136 connected to a portion of the proximal interface 110, as will be described in further detail below, to a distal end 138 connected to a corresponding one of the jaws 108. In an exemplary embodiment, the control members 116 are formed as flexible strands, filaments or coils formed of, for example, a metal or polymer. The distal end 138 of each of the control members 116 in this embodiment is attached to the corresponding one of the jaws 108 so that longitudinal movement of the control members 116 relative to the catheter 104 correspondingly moves the grasper 102 between the open and closed configurations.

Each control member 116 in this embodiment is movably received within an outer shaft 140 extending along an exterior length of the catheter 104 from a proximal end 142 proximate the proximal interface 110 to a distal end 144. In an exemplary embodiment, the device 100 comprises a pair of shafts 140 fixed along opposing longitudinal sides of the catheter 104 so that a corresponding one of the control members 116 received is longitudinally slidable therein as the control members 116 are moved proximally and distally relative to the catheter 104. Distal ends 144 of the shafts 140 are positioned along the catheter 104 so that the distal ends 138 of the control members 116 extend distally past the distal ends 144 of the outer shafts 140 to be connected to the jaws 108 of the grasper 102 when it is mounted over the distal end 106 of the catheter 104 and when it is moved distally off of the catheter 104 to grasp and sever a portion of a thrombus.

Figure 6:
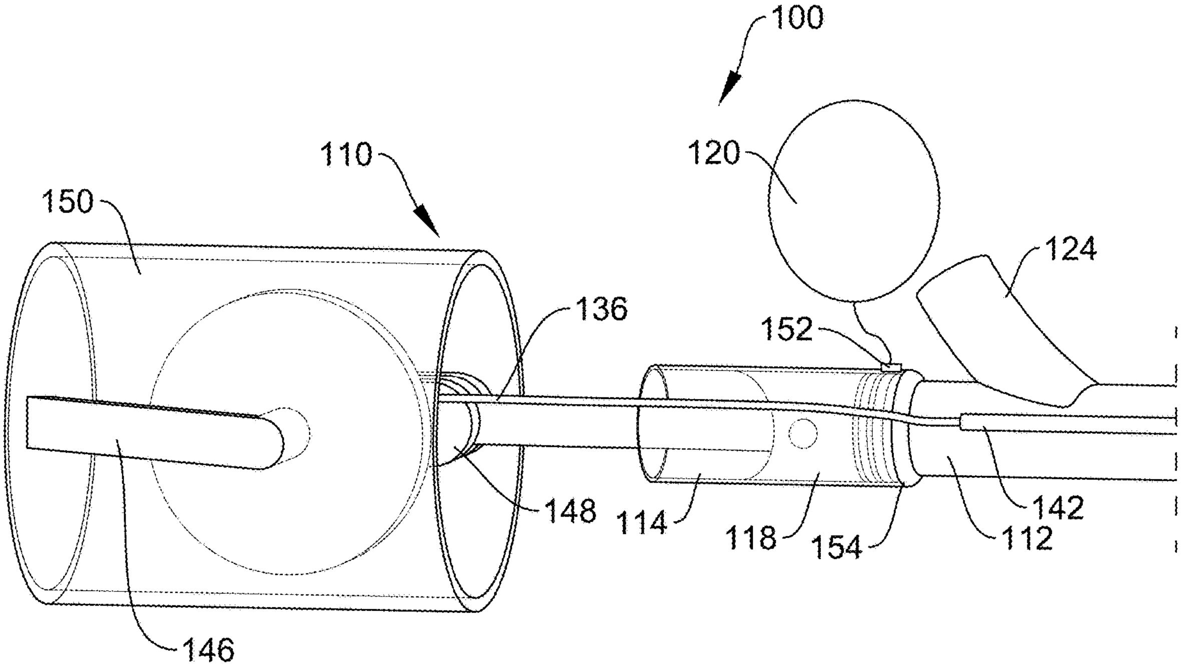
FIG. 6 shows a partially transparent perspective view of a proximal portion of the device according to FIG. 1, when the device is in the open configuration.
Figure 7:
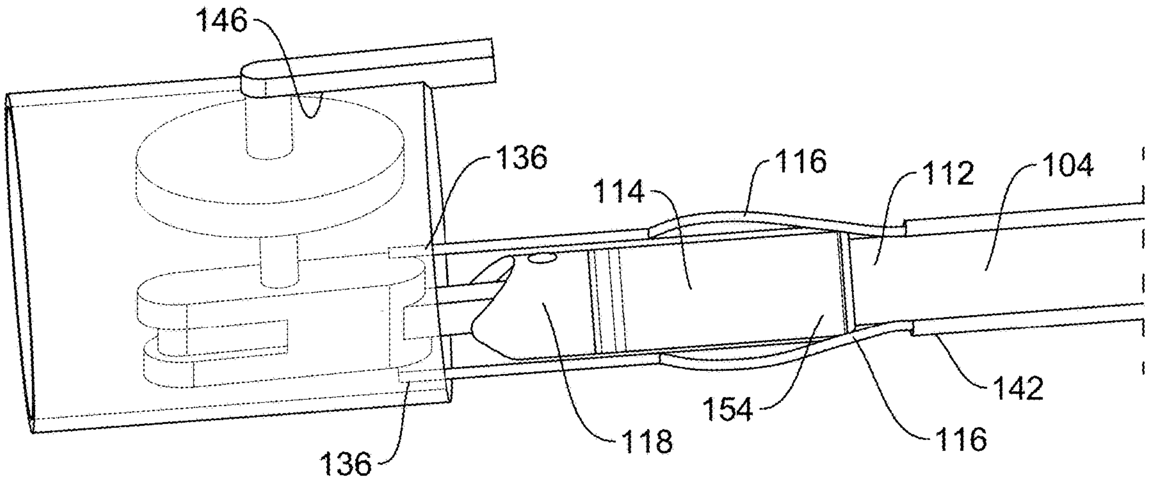
FIG. 7 shows a partially transparent side view of the proximal portion of the device according to FIG. 1, when the device is in the closed configuration.

According to an exemplary embodiment, as shown in FIGS. 6-7, the proximal interface 110 includes an actuator such as, for example, a rotating handle 146 connected to the proximal ends 136 of the control members 116 and the piston 118 via a crank shaft 148. The rotating handle 146 is rotatable relative to a proximal housing 150 within which the crank shaft 148 is housed. As described above, the piston 118 is movably received within a cylindrical housing 114 connected to the proximal end 112 of the catheter 104. The cylindrical housing 114 is in fluid communication with the lumen 122 of the catheter 104 so that, as described below, negative pressure may be applied through the lumen 122 via a movement of the piston 118 within the cylindrical housing 114, to remove the grasped and separated portion of the thrombus from the blood vessel. The proximal interface 110 further includes a thrombus collecting bag 120 connected to the cylindrical housing 114 so that the separated portion of thrombus may be subsequently collected in the thrombus collecting bag 120. The thrombus collecting bag 120 may be connected to the cylindrical housing 114 via a one-way valve 152 so that, upon collection of the separated portion of thrombus therein, the collected thrombus cannot reenter the housing 114.

In particular, the one-way valve 154 connecting the thrombus collecting bag 120 to the cylindrical housing 114 permits passage of the separated portion 12 of thrombus 10 from the cylindrical housing 114 to the thrombus collecting bag 120, but does not permit passage of any portion of the thrombus from the thrombus collecting bag 120 to the cylindrical housing 114. Although the exemplary embodiments show and describe the thrombus as being collected in the collecting bag 120, it will be understood by those of skill in the art that the thrombus may be collected in any container or storage vessel connected to the cylindrical housing 114.

The rotating handle 146 is connected to the crank shaft 148 such that rotation of the handle 146 correspondingly rotates the crank shaft 148. In the open configuration, the piston 118 is positioned at a distal end of the cylindrical housing 114, as shown in FIG. 6. The proximal ends 136 of the control members 116 and the piston 118 are connected to the crank shaft 148 so that when the rotating handle 146 is rotated to move the control members 116 distally relative to the catheter 104, the piston 118 is simultaneously moved proximally within the cylindrical housing 114, as shown in FIG. 7, applying negative pressure within the lumen 122. Thus, as the grasper 102 is moved distally off of the distal end 106 of the catheter 104 and reverts under its natural bias from the open configuration toward the closed configuration to grasp and separate a portion of the thrombus from a remaining portion of the thrombus, the negative pressure applied within the catheter 104 draws the grasped and separated portion of the thrombus proximally through the catheter 104 into the cylindrical housing 114.

Further rotation of the rotating handle 146 will then rotate the crank shaft 148 such that the control members 116 are moved proximally relative to the catheter 104 to pull the grasper 102 back onto the distal end 106 of the catheter 104 toward the open configuration. This same rotation of the rotating handle 146 also moves the piston 118 distally within the cylindrical housing 114 to remove the negative pressure applied within the lumen 122 and push the separated portion of thrombus from the cylindrical housing into the thrombus collecting bag 120.

The rotating handle 146 may be repeatedly and/or continuously rotated relative to the proximal housing 150, as described above, to systematically move the grasper 102 between the open and closed configurations, grasping, separating, and removing portions of the target thrombus, until the entirety of the target thrombus has been removed from the blood vessel.

Figure 8:
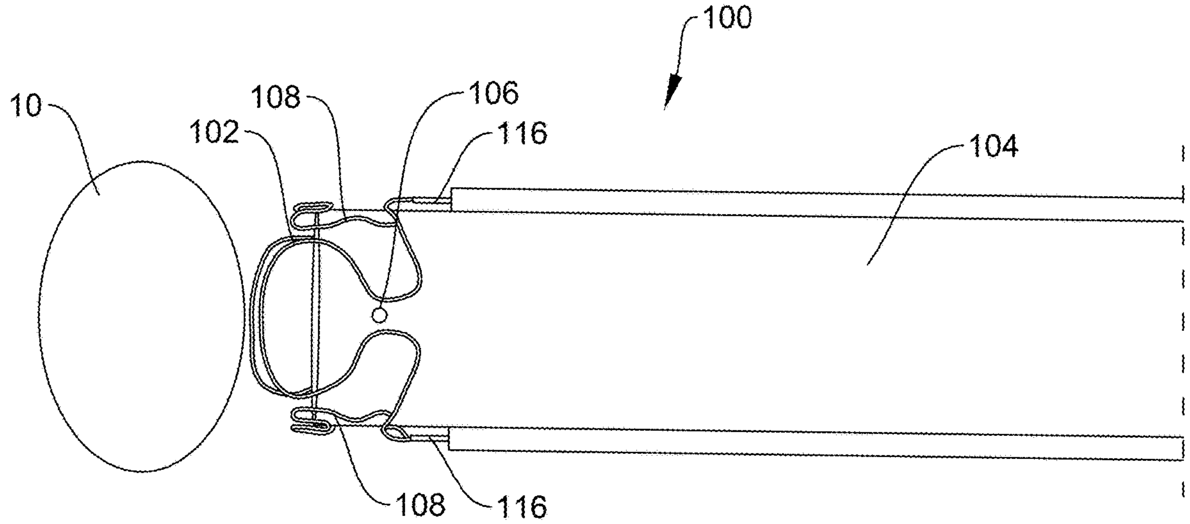
FIG. 8 shows a side view of the distal portion of the device of FIG. 1, in a target blood vessel in the open configuration.
Figure 9:
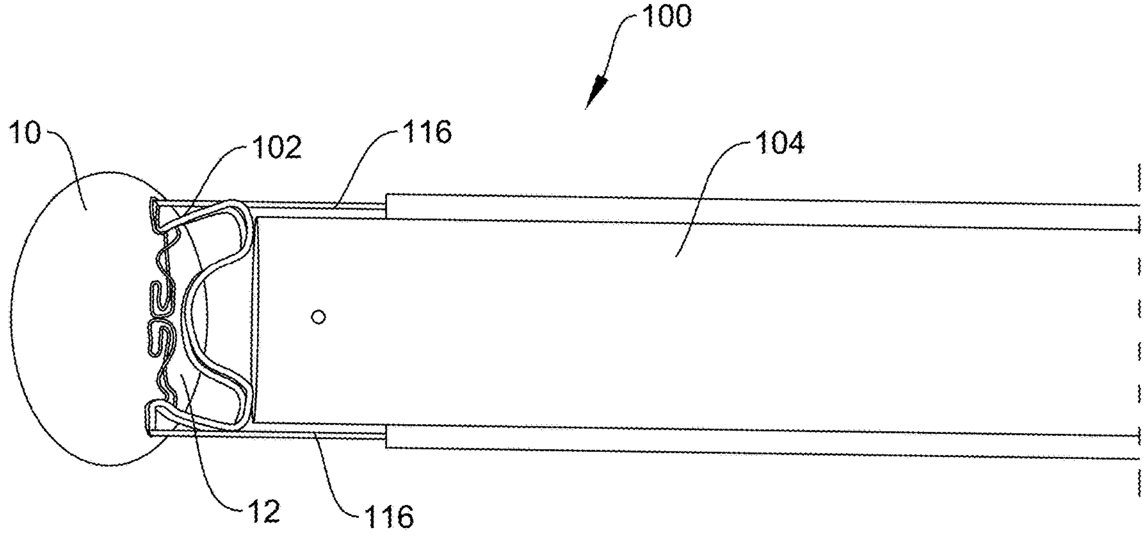
FIG. 9 shows a side view of the distal portion of the device of FIG. 1, grasping a portion of a target thrombus in the closed configuration.
Figure 10:
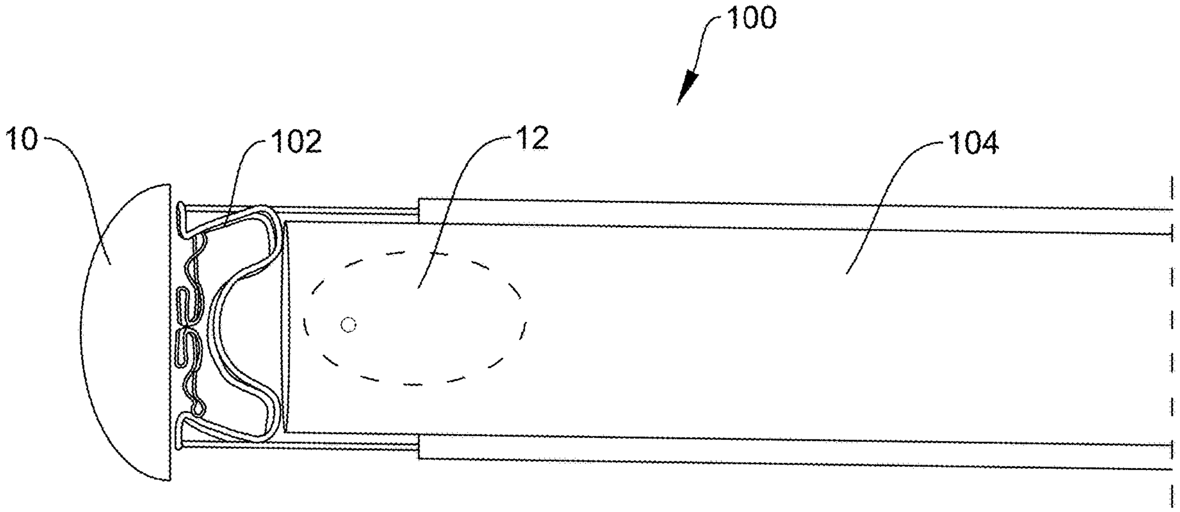
FIG. 10 shows a side view of the distal portion of the device of FIG. 1, the grasped portion of thrombus separating from a remaining portion thereof.
Figure 11:
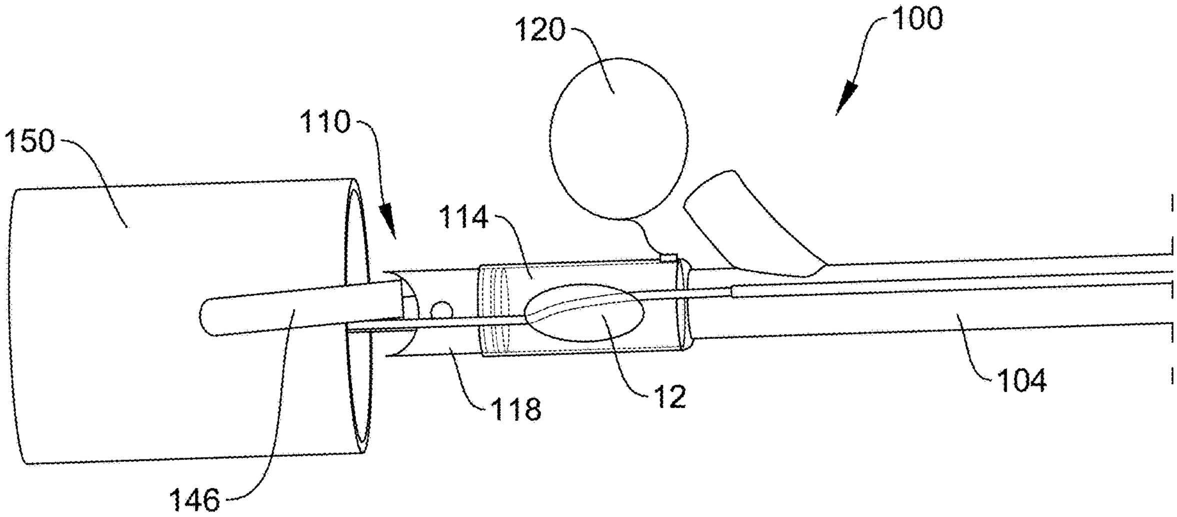
FIG. 11 shows a side view of the proximal portion of the device of FIG. 1, the separated portion of thrombus received in a cylindrical housing of the proximal portion of the device.

FIGS. 8-13 show an exemplary method for performing a thrombectomy utilizing the device 100. As shown in FIG. 8, the grasper 102, mounted over the distal end 106 of the catheter 104 in the open configuration, is inserted through a blood vessel to a target area in the blood vessel under image guidance until the grasper 102 is positioned adjacent and/or against a target thrombus 10. Once the grasper 102 is positioned adjacent the target thrombus 10 as desired, the rotating handle 146 is rotated relative to the proximal housing 150 to move the control members 116 distally relative to the catheter 104 moving the grasper 102 distally off of the distal end 106 of the catheter 104 so that the jaws 108 move from the open configuration toward the closed configuration, as shown in FIG. 9. As the grasper 102 moves toward the closed configuration, the jaws 108 grasp a portion 12 of the target thrombus 10 positioned therebetween so that teeth 132 penetrate the thrombus 10 and separate the grasped portion 12 from a remaining portion of the thrombus 10. As described above, while the control members 116 are moving distally relative to the catheter 104, the piston 118 moves distally within the cylindrical housing 114, applying a negative pressure within the lumen 122. This draws the separated portion 12 of thrombus 10 proximally through the catheter 104, as shown in FIG. 10, and into the cylindrical housing 114, as shown in FIG. 11.

Figure 12:
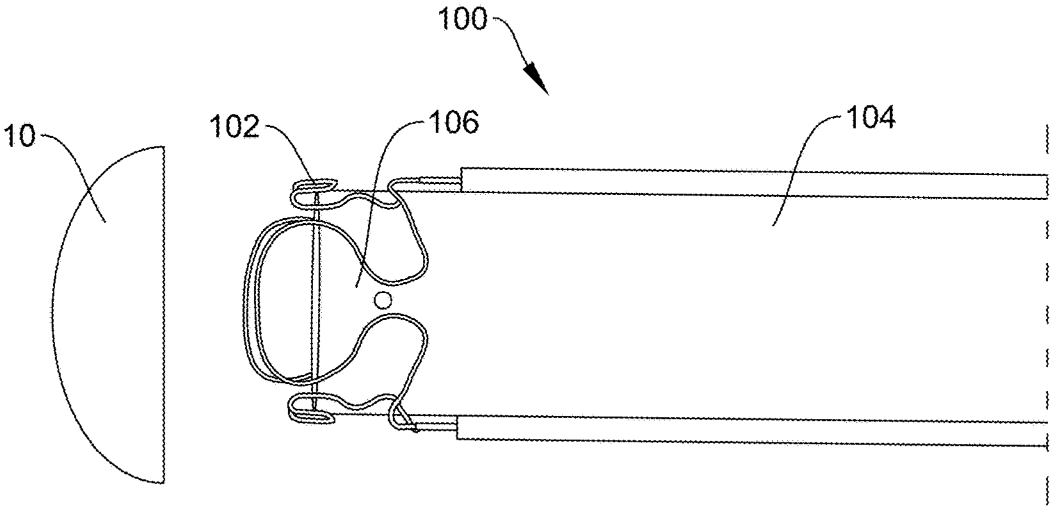
FIG. 12 shows a side view of the distal portion of the device of FIG. 1, the grasper moved back toward the open configuration.
Figure 13:
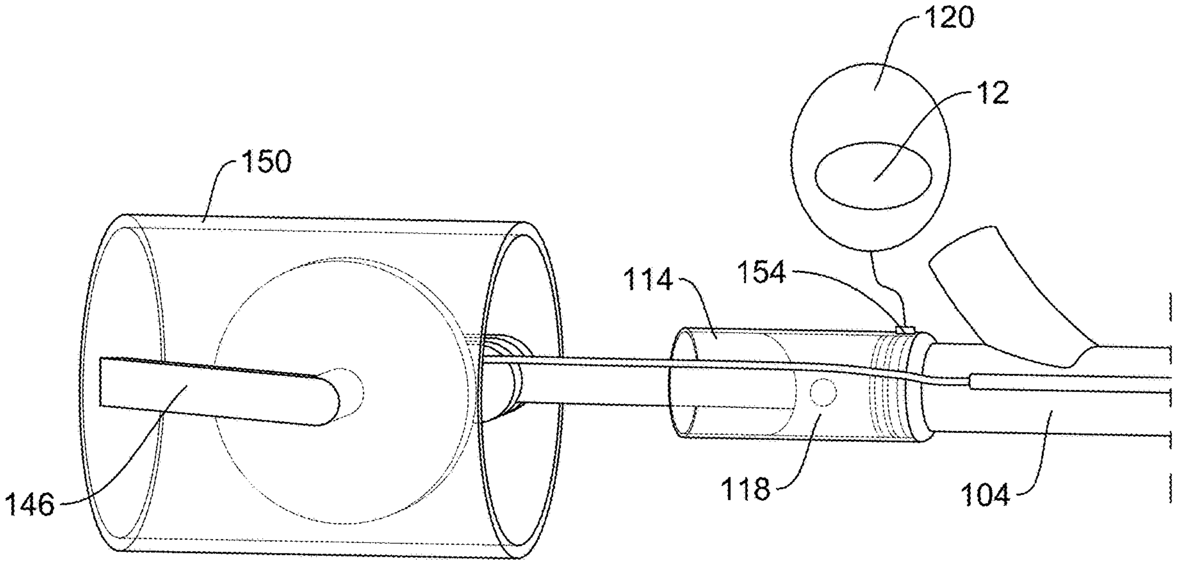
FIG. 13 shows a side view of the proximal portion of the device of FIG. 1, the separated portion of thrombus received in a thrombus collecting bag of the proximal portion of the device.

Once the separated portion of thrombus 12 has been received within the cylindrical housing 114, the user further rotates the handle 146 relative to the proximal housing 150 correspondingly rotating the crank shaft 148 so that the control members 116 move proximally relative to the catheter 104 pulling the grasper 102 proximally over the distal end 106 of the catheter 104 from the closed configuration to the open configuration, as shown in FIG. 12. While the control members 116 are being moved proximally relative to the catheter 104, the piston 118 is simultaneously moved distally within the cylindrical housing 114, removing the negative pressure within the lumen 122 and pushing the separated portion 12 of thrombus 10 from the cylindrical housing 114 to the thrombus collecting bag 120 via the one-way valve 154, as shown in FIG. 13.

The user may then continue to move the grasper 102 between the open configuration and the closed configuration via rotation of the rotation handle 146 relative to the proximal housing 150, while moving the device 100 distally through the target blood vessel so keep the remaining portion of the thrombus positioned as desired adjacent to the distal end 106 of the catheter 104.

The grasper 102 continues to grasp and separate portions of the target thrombus, collecting these portions of the thrombus with each iteration (e.g., with each rotation of the rotation handle 146), until the entire target thrombus has been removed from the blood vessel and collected in the thrombus collecting bag 120. It will be understood by those of skill in the art that the rotation handle 146 may be rotated in a continuous manner as the catheter 104 is simultaneously repositioned (as necessary) so that the grasper 102 systematically "bites" and "swallows" portions of the remaining thrombus until the entire thrombus has been removed. Upon removal of the entire target thrombus, the device 100 may be removed from the target blood vessel.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A method for performing a thrombectomy, comprising:

inserting a catheter through a blood vessel until a grasper mounted over a distal end of the catheter in an open configuration is adjacent a target thrombus within the blood vessel, first and second jaws of the grasper extending over opposing portions of the catheter in the open configuration so that a first portion of the thrombus is received between the first and second jaws;

moving the grasper toward a closed configuration so that the grasper is moved distally off of the catheter and the first and second jaws are moved toward one another to grasp the first portion of the thrombus received therebetween, thereby separating the first portion of the thrombus from a remaining portion of the thrombus, a negative pressure applied through the catheter as the grasper is moved toward the closed configuration so that the first portion of the thrombus is drawn proximally through the catheter; and moving the grasper toward the open configuration by drawing the grasper proximally over the distal end of the catheter, the first portion of the thrombus escaping into a thrombus collecting bag as the grasper is moved toward the open configuration.

2. The method of claim 1, further comprising:

moving the catheter, with the grasper mounted thereover in the open configuration, distally within the blood vessel so that a second portion of the thrombus is received between the first and second jaws of the grasper;

moving the grasper toward the closed configuration so that the grasper is moved distally off of the catheter and the first and second jaws are moved toward one another to grasp the second portion of the thrombus received therebetween, thereby separating the second portion of the thrombus from the remaining portion of the thrombus, the negative pressure applied through the catheter as the grasper is moved toward the closed configuration so that the second portion of the thrombus is drawn proximally through the catheter; and moving the grasper toward the open configuration by drawing the grasper proximally over the distal end of the catheter, the second portion of the thrombus escaping into the thrombus collecting bag as the grasper is moved toward the open configuration.

3. The method of claim 1, wherein teeth of the first and second jaws penetrate the first portion of the thrombus as the grasper is moved toward the closed configuration to separate the first portion of the thrombus from the remaining portion of the thrombus.

4. The method of claim 1, wherein the negative pressure is applied through the catheter via a piston moving proximally within a cylindrical housing connected to a proximal end of the catheter so that the first portion of the thrombus is drawn proximally into the cylindrical housing.

5. The method of claim 4, wherein the first portion of the thrombus escaped into the thrombus collecting bag as the piston is moved distally within the cylindrical housing.

6. The method of claim 4, wherein the piston and the cylindrical housing are part of a proximal interface, the proximal interface further including a crank shaft connected to the piston and a proximal end of a first control member.

7. The method of claim 6, wherein a distal movement of the first control member relative to the catheter moves the grasper toward the closed configuration and a proximal movement of the first control member relative to the catheter moves the grasper toward the open configuration.

8. The method of claim 7, wherein the distal movement of the first control member relative to the catheter moves the piston proximally within the cylindrical housing to create the negative pressure and the proximal movement of the first control member relative to the catheter moves the piston distally within the cylindrical housing.

9. The method of claim 6, wherein the proximal interface further includes a rotating handle connected to the crank shaft so that a rotation of the rotating handle moves the grasper between the open and closed configurations.

10. The method of claim 1, wherein a first control member connected to the first jaw of the grasper is moved longitudinally relative to the catheter to move the grasper between the open and closed configurations.

11. The method of claim 10, wherein a second control member connected to the second jaw of the grasper is moved longitudinally relative to the catheter to move the grasper between the open and closed configurations.

12. The method of claim 11, wherein the first control member extends through a first outer shaft and the second control member extends through a second outer shaft, the first and second outer shafts extending longitudinally along an exterior surface of the catheter.

13. The method of claim 1, wherein the first and second jaws of the grasper are connected to one another via hinges that bias the grasper toward the closed configuration so that the first and second jaws are maintained in the open configuration via an exterior surface of the catheter when the grasper is mounted over the catheter and revert toward the closed configuration when the grasper is moved distally off of the catheter.

14. The method of claim 1, wherein the grasper includes a covering extending over portions of each of the first and second jaws to define a substantially solid surface thereof so that any portions of the thrombus grasped between the first and second jaws are prevented from escaping distally therefrom.

* * * * *